United States Patent [19]

Ryan

[11] Plant 4,427

[45] Jun. 12, 1979

[54] IMPATIENS PLANT — MOHAWK

[76] Inventor: John J. Ryan, 39877 Sundale Dr., Fremont, Calif. 94538

[21] Appl. No.: 921,998

[22] Filed: Jul. 3, 1978

[51] Int. Cl.[2] ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant, known by the cultivar name Mohawk, and discovered by me in commercial greenhouses in Fremont, Calif. Mohawk is not close to any commercial varieties. Mohawk is particularly characterized by a slightly dark foliage with no variegation, which reddens slightly under high light, a medium size red-purple flower, very floriferous, and a spreading growth habit.

1 Drawing Figure

BACKGROUND OF THE INVENTION

The present new variety (seedling) was discovered by me in a commercial greenhouse in Fremont, Calif. as a result of the cross pollination of the unpatented pistil parent 76-68-1 and the patented pollen parent 76-22-1 (Chickasaw), U.S. Plant Pat. No. 4,260.

Asexual reproduction of my new cultivar by terminal or stem cuttings grown in pots in a plastic (polyethylene) greenhouse in Fremont, Calif. under normal environmental conditions show that the characteristics described come true to form and are established and transmitted through succeeding propagations.

Color readings were taken during daylight hours in full sun, and all colors are based on the Royal Horticultural Society Colour Chart.

BRIEF SUMMARY

Mohawk is not close to any commercial variety. The following are outstanding characteristics of Mohawk:

1. Slightly dark foliage;
2. Very floriferous;
3. Medium size red-purple flower; and
4. No variegation of foliage.

DESCRIPTION OF THE PHOTOGRAPH

The accompanying colored photograph illustrates the overall appearance of the cultivar Mohawk, showing flower color under high light conditions. Under lower light the flower is darker.

DETAILED DESCRIPTION

The following detailed description of Mohawk was based on observations made of the new cultivar on Oct. 26, 1977:

I. PLANT

Name: Mohawk.
Origin: Seedling of the cross pollination of the unpatented pistil parent 76-68-1 and the patented pollen parent 76-22-1 (Chickasaw), U.S. Plant Pat. No. 4,260.
Form: Upright to spreading.
Height to flowering: 30 cm.
Growth: Fast.
Type of cutting: Terminal or stem.
Rooting time: Typical, 10–14 days.

Rooting habit: Fast, dendritic.

II. FOLIAGE

Arrangement: Lower leaves of any break opposite (usually one set); upper foliage of any break whorls of 3 to 5.
Shape: Oblanceolate to lanceolate.
Tip: Acuminate.
Base: Attenuate.
Margin: Serrulate.
Veination: Pinnate.
Size: Blade and petals 6.5 cm. to 10.0 cm.; length of blade 6.0 cm. to 8.5 cm.; width of blade at widest point 2.5 cm. to 3.5 cm.
Surface: Glabrous.
Variegation: None.
Color:

1. *Petiole.*—48 B to 48 C.
2. *Veins.*—48 C, but lightens.
3. *Leaf.*—a. Upper 137 B with some red, depending on light intensity. b. Lower 194 A to 194 B with an overlay of 184 B.

III. STEM

Color: 144 D.
Internode:

1. *Length.*—Moderate.
2. *Size.*—Moderate.

Node expanded (relative to internode): Little, if any.
Breaking action: Moderate.

IV. FLOWER

Form: Typical.
Borne: End of branches, terminal.
Blooming habit:

1. *Relative number.*—Profuse.
2. *Time to flowering.*—Short.
3. *Longevity.*—Typical, 3 to 5 days.

Size of mature flower: First flower on a plant may be small.

1. *Length.*—5.0 cm. to 6.0 cm.
2. *Width.*—5.0 cm. to 5.5 cm.
3. *Spur.*—4.5 cm. to 5.5 cm.

Color: Lightens under high heat and light.

1. *Eye.*—57 A.

-continued

| | |
|---|---|
| 2. Middle: | 67 B to 67 C, depending on flower age and light intensity |
| 3. Edge: | |

Pedicel: 53 D for red on upper side, 145 C for green on upper and lower side.

V. REPRODUCTIVE ORGANS

Stamen:

| | |
|---|---|
| 1. Anthers | Typical, fused hood over pistil |
| 2. Filaments | |

3. *Pollen.*—a. Color: 158 C. b. Abundance: Typical, plenty.

Pistils:

| | |
|---|---|
| 1. Style | Typical, but top of ovary just above stigma is colored 187 A |
| 2. Ovaries | |

I claim:

1. A new and distinct form of Impatiens plant as described and illustrated, known by the cultivar name Mohawk, and particularly characterized by slightly reddened foliage under high light, very floriferous, a medium size red-purple flower, and no variegation of foliage.

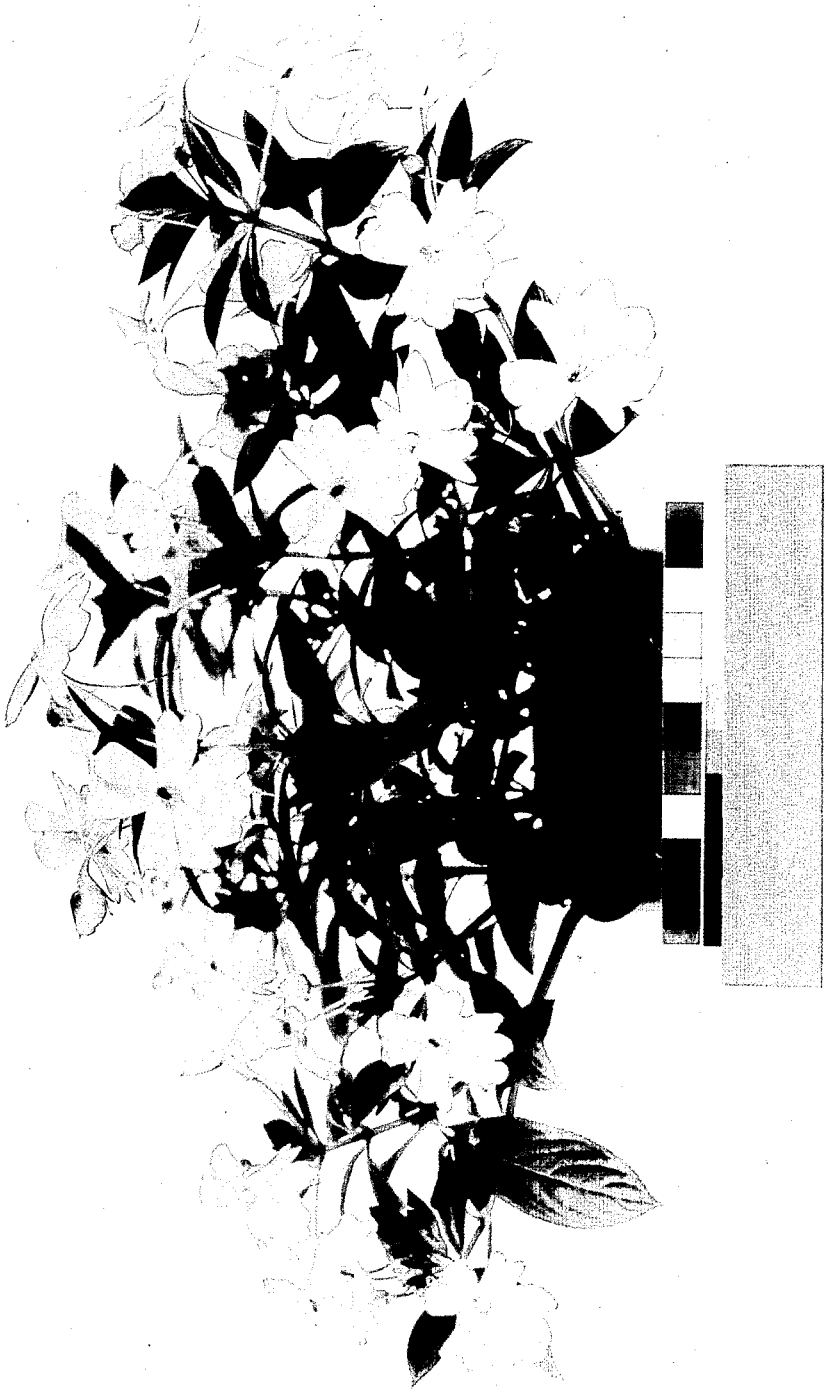

* * * * *